(12) United States Patent
Eisinger

(10) Patent No.: US 11,534,173 B2
(45) Date of Patent: Dec. 27, 2022

(54) SURGICAL STAPLING INSTRUMENT WITH TELESCOPIC TROCAR ASSEMBLY

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 144 days.

(21) Appl. No.: 17/176,320

(22) Filed: Feb. 16, 2021

(65) Prior Publication Data

US 2021/0275179 A1 Sep. 9, 2021

Related U.S. Application Data

(60) Provisional application No. 62/986,111, filed on Mar. 6, 2020.

(51) Int. Cl.
*A61B 17/115* (2006.01)
*A61B 17/34* (2006.01)
*A61B 17/00* (2006.01)

(52) U.S. Cl.
CPC .......... *A61B 17/1155* (2013.01); *A61B 17/34* (2013.01); *A61B 2017/00991* (2013.01)

(58) Field of Classification Search
CPC ..................... A61B 17/1155; A61B 17/34
See application file for complete search history.

(56) References Cited

U.S. PATENT DOCUMENTS

| | | | |
|---|---|---|---|
| 7,303,106 B2 | 12/2007 | Milliman et al. | |
| 8,801,735 B2 | 8/2014 | Shelton, IV et al. | |
| 9,010,605 B2 | 4/2015 | Olson et al. | |
| 9,987,001 B2 * | 6/2018 | Williams | A61B 17/105 |
| 10,080,566 B2 | 9/2018 | Milliman | |
| 2014/0326777 A1 * | 11/2014 | Zingman | A61B 17/1155 |
| | | | 227/175.2 |
| 2019/0105051 A1 * | 4/2019 | Swayze | A61B 17/115 |
| 2019/0343517 A1 | 11/2019 | Zemlok et al. | |
| 2019/0380714 A1 | 12/2019 | Chen et al. | |
| 2020/0015820 A1 | 1/2020 | Contini et al. | |

* cited by examiner

*Primary Examiner* — Nathaniel C Chukwurah
(74) *Attorney, Agent, or Firm* — Carter, DeLuca & Farrell LLP

(57) ABSTRACT

A surgical stapling instrument includes an adapter assembly having a trocar assembly transitionable between extended and retracted configurations. The trocar assembly includes a first member rotatably supporting a lead screw, a second member, and a third member slidable relative to the second member. The second member is operatively coupled to the lead screw such that rotation of the lead screw causes axial displacement of the second member relative to the first member. The third member includes a trocar engageable with the anvil assembly for axial displacement therewith. The third member is transitionable between an engaged state, in which, the third member is operatively coupled to the lead screw such that rotation of the lead screw causes axial displacement of the third member relative to the second member, and a disengaged state, in which, the third member is operatively disengaged from the lead screw.

20 Claims, 8 Drawing Sheets

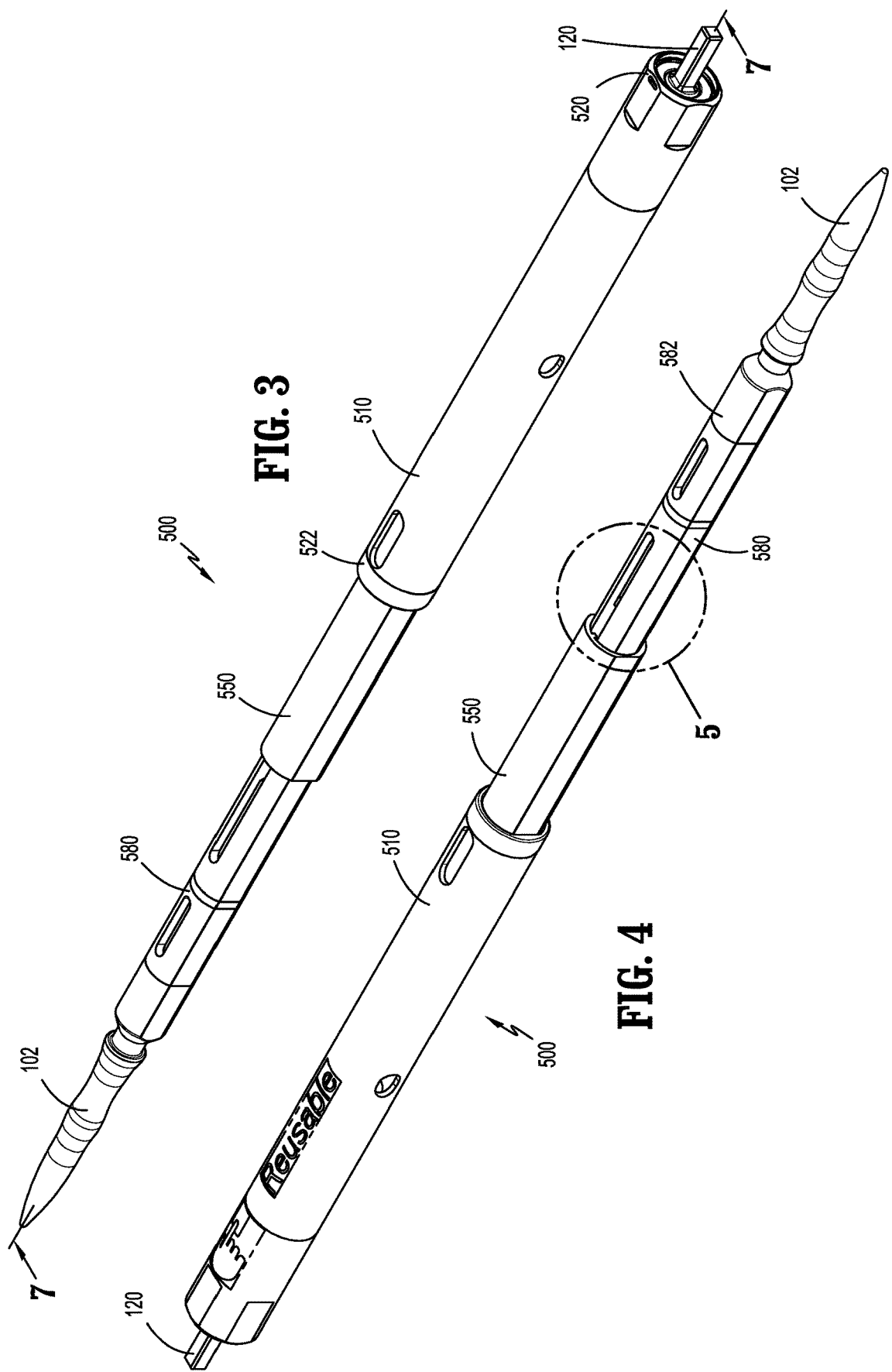

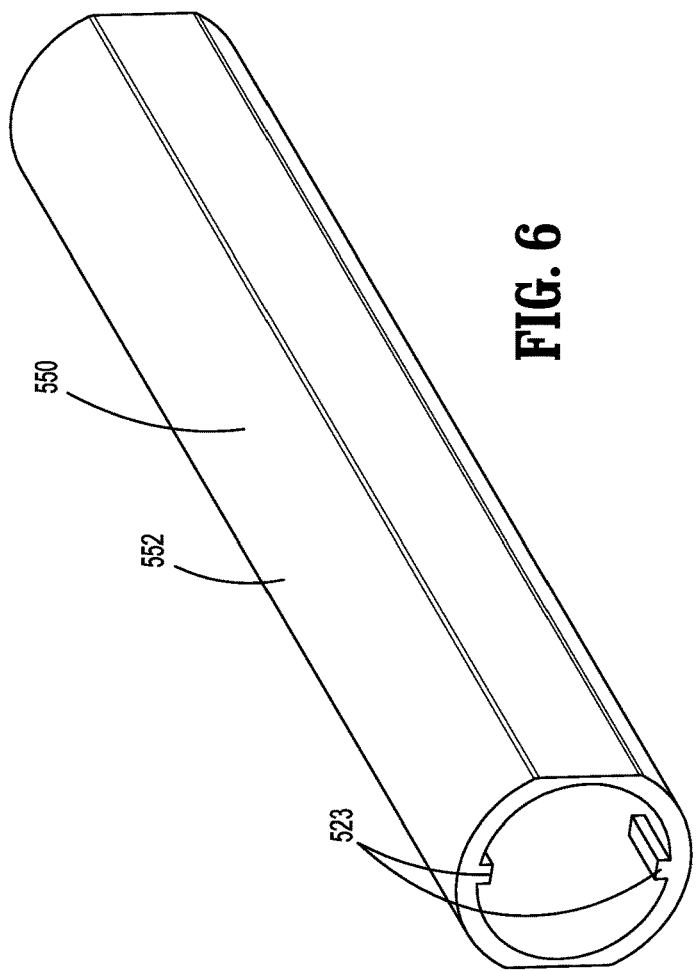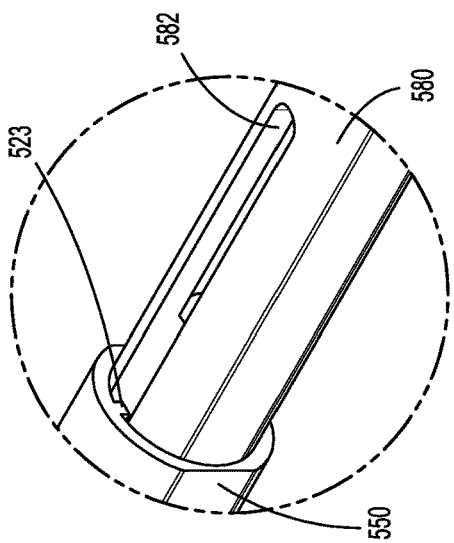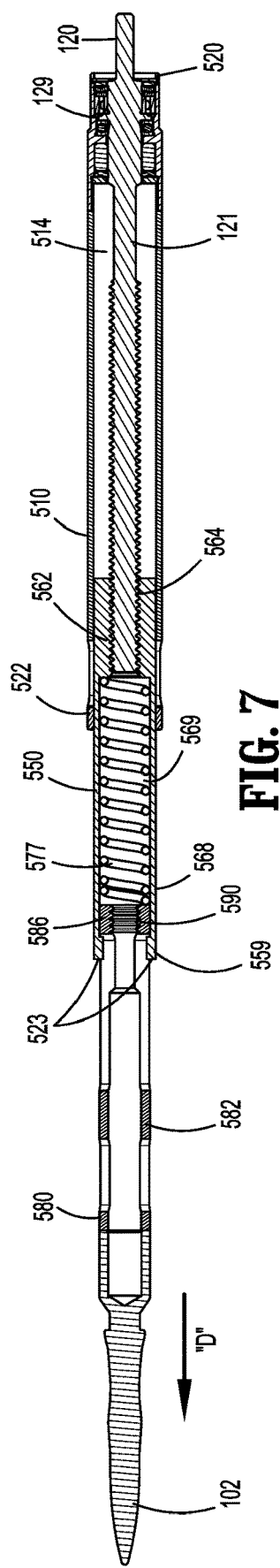

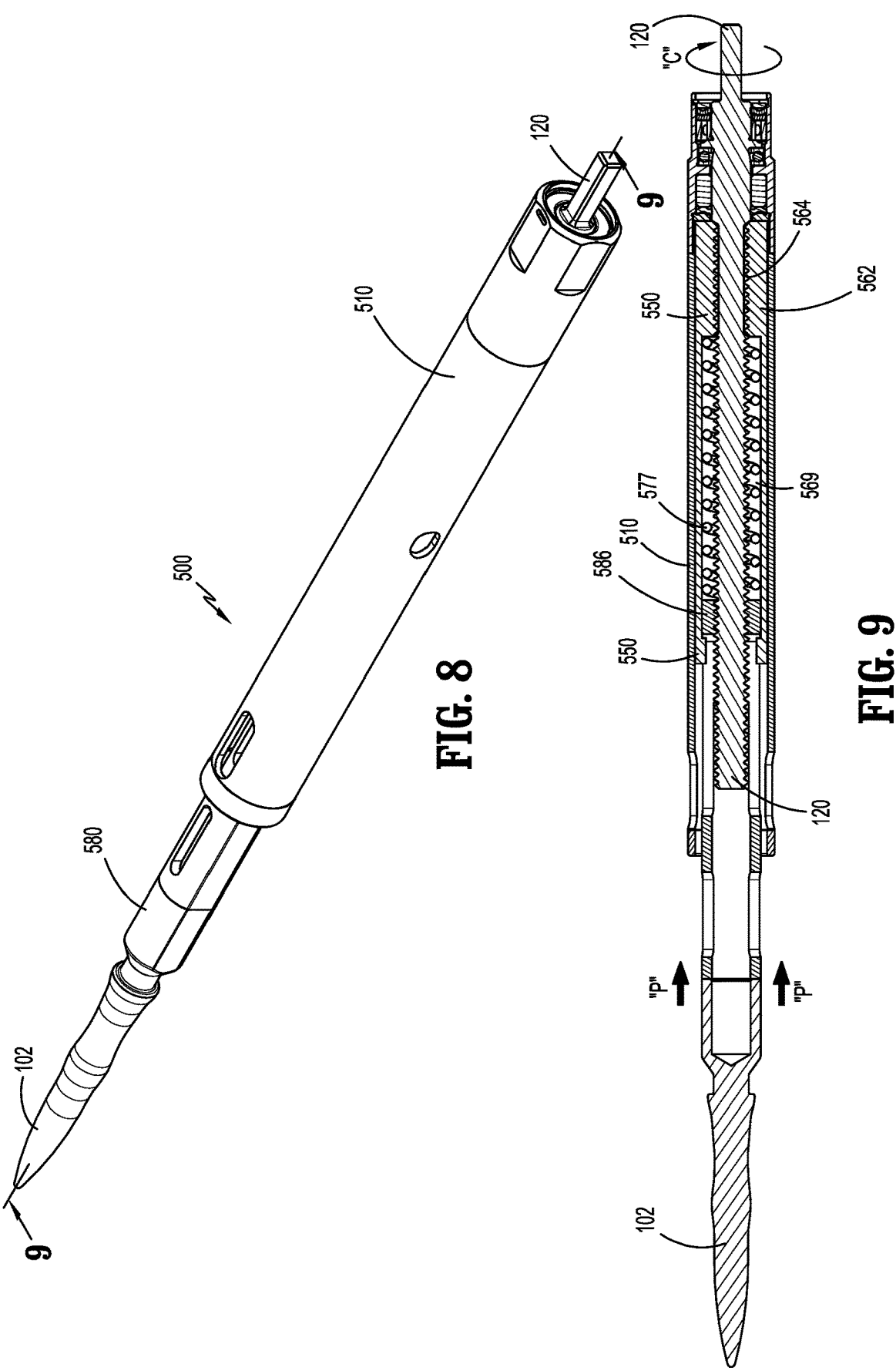

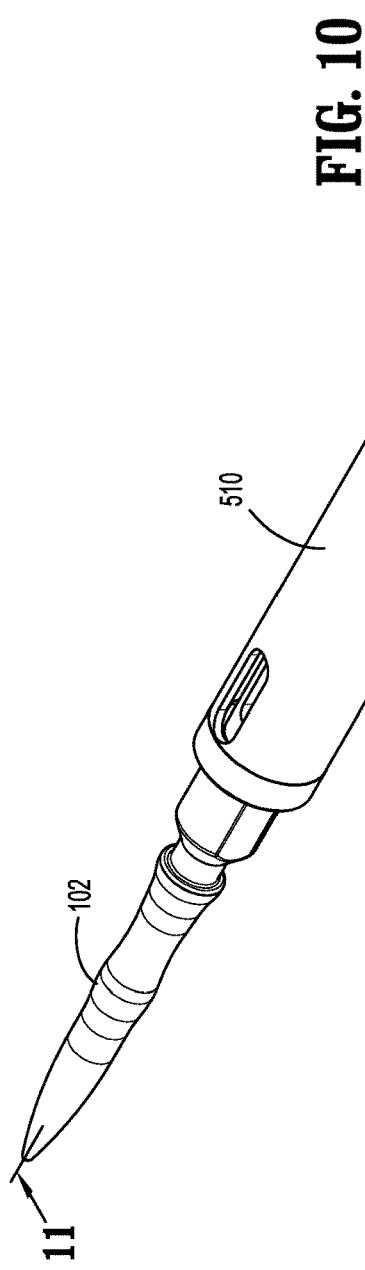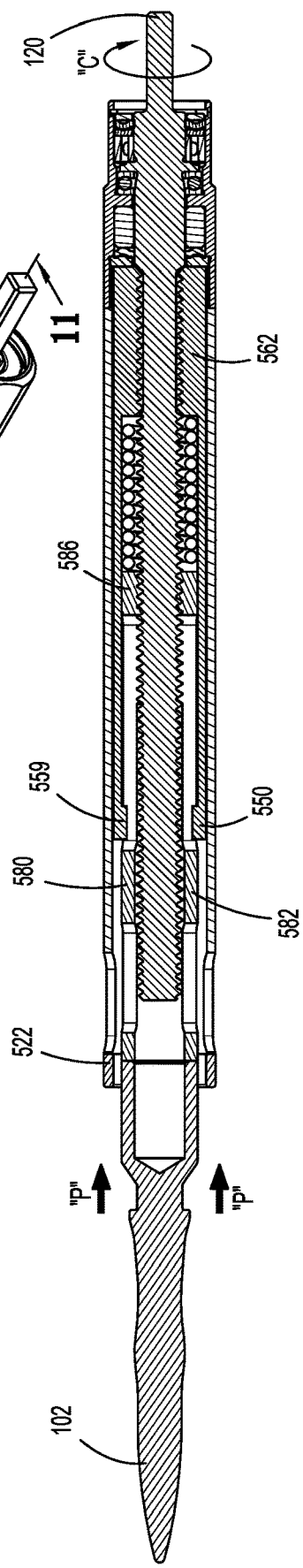

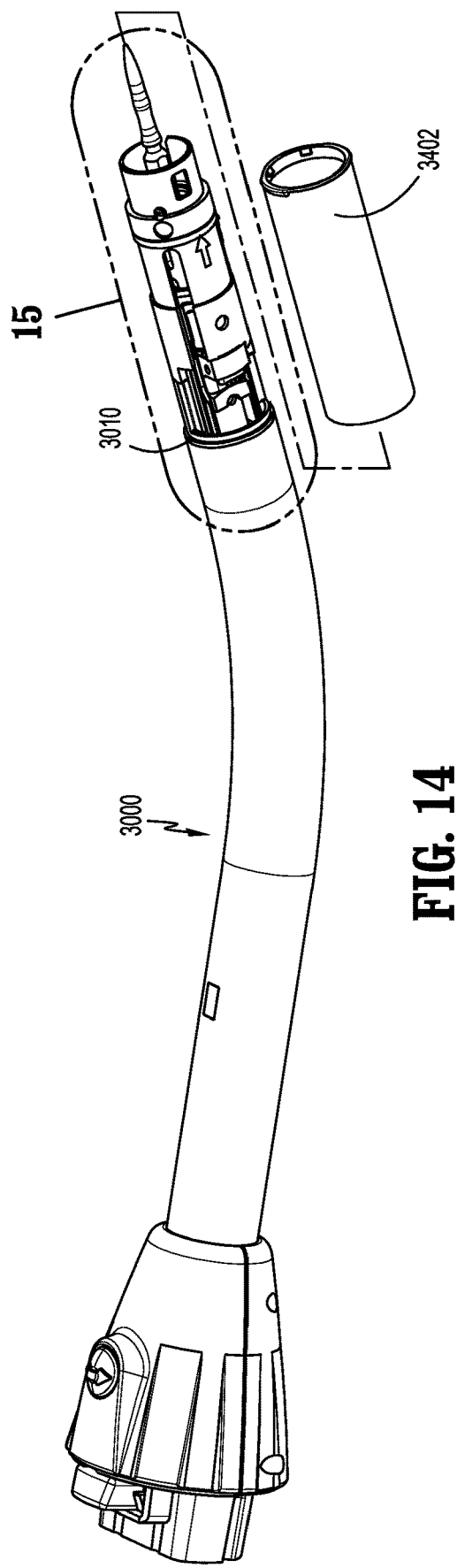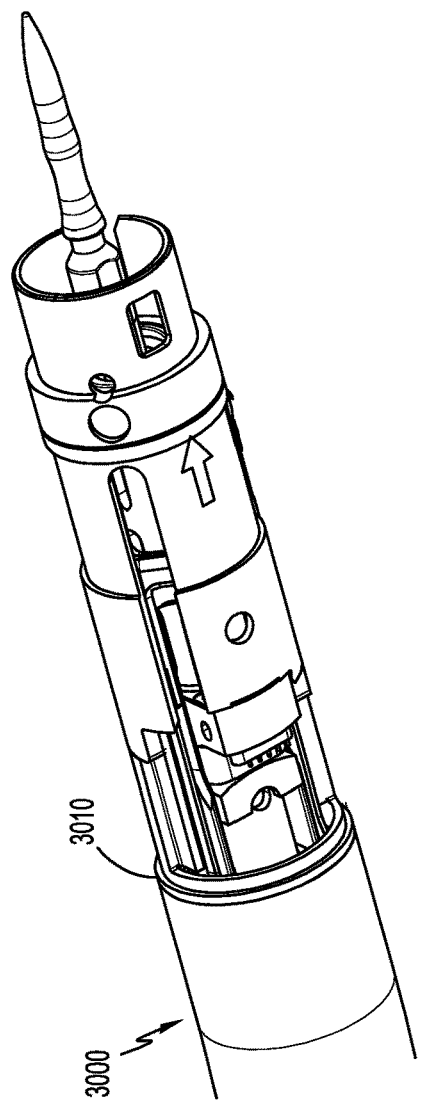

SURGICAL STAPLING INSTRUMENT WITH TELESCOPIC TROCAR ASSEMBLY

CROSS-REFERENCE TO RELATED APPLICATIONS

This application claims the benefit of and priority to U.S. Provisional Patent Application Ser. No. 62/986,111, filed Mar. 6, 2020, the disclosure of which is incorporated by reference herein in its entirety.

FIELD

The disclosure relates generally to surgical stapling instruments, and more particularly, to a surgical stapling instrument with a telescopic trocar assembly.

BACKGROUND

Anastomosis is the surgical joining of separate hollow organ sections. Typically, an anastomosis procedure follows surgery in which a diseased or defective section of hollow tissue is removed, and the end sections are stapled via a surgical stapling instrument. Depending on the desired anastomosis procedure, the end sections may be joined by circular or side-to-side organ reconstruction methods, for instance.

In a circular anastomosis procedure, the two ends of the organ sections are joined by means of a surgical stapling instrument which drives a circular array of staples through the end section of each organ section and simultaneously cores any tissue interior of the driven circular array of staples to free the tubular passage. Typically, these surgical stapling instruments include an elongated body portion having a handle portion at a proximal end to actuate the surgical stapling instrument and a staple holding component disposed at a distal end. An anvil assembly including an anvil retention rod with an attached anvil head is mounted to a trocar assembly at the distal end of the surgical stapling instrument adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are formed by the anvil head. An annular knife is advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a surgical stapling instrument for hemorrhoid treatment, the anvil head and the staple holding-component of the surgical stapling instrument are inserted through the anus and into the rectum with the anvil head and the staple-holding component in an open or spaced part position. Thereafter, a purse string suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly is engaged with the anvil retention rod. The surgical stapling instrument is fired to remove the hemorrhoidal tissue and staple the tissue.

SUMMARY

In accordance with the disclosure, a surgical stapling instrument includes an anvil assembly, a shell assembly, and an adapter assembly. The anvil assembly includes an anvil head and an anvil center rod extending proximally from the anvil head. The shell assembly includes an annular staple cartridge including a plurality of staples. The adapter assembly includes a tubular shaft supporting the shell assembly at a distal portion of the tubular shaft, and a trocar assembly transitionable between an extended configuration and a retracted configuration. The trocar assembly includes a lead screw adapted to be coupled to an actuator for rotational input, a first member rotatably supporting the lead screw, a second member, and a third member. The second member is operatively coupled to the lead screw such that rotation of the lead screw causes axial displacement of the second member relative to the first member. The third member is slidable relative to the second member. The third member includes a trocar detachably engageable with the anvil center rod for axial displacement therewith. The third member is transitionable between an engaged state, in which, the third member is operatively coupled to the lead screw such that rotation of the lead screw causes axial displacement of the third member relative to the second member, and a disengaged state, in which, the third member is operatively disengaged from the lead screw. Rotation of the lead screw transitions the trocar assembly between the extended configuration and the retracted configuration.

In an aspect, the first, second, and third members may be concentrically arranged.

In another aspect, the lead screw may include an annular protrusion configured to be received in a circular groove defined in an inner surface of the first member to inhibit axial displacement of the lead screw during rotation thereof.

In yet another aspect, the second member may include a first engaging portion that defines a first threaded bore. The first threaded bore may be engageable with the lead screw.

In an aspect, the first engaging portion of the second member may be disposed in a proximal end portion of the second member.

In another aspect, the second member may further include a receiving portion distal of the engaging portion. The receiving portion may define a first channel configured to slidably receive the third member therein.

In yet another aspect, the third member may include a second engaging portion slidably disposed within the second member. The second engaging portion may define a second threaded bore configured to threadably engage the lead screw.

In still yet another aspect, the second member may include a spring member interconnecting the first engaging portion of the second member and the second engaging portion of the third member.

In still yet another aspect, the spring member may be configured to bias the third member distally when the second engaging portion of the third member is disengaged from the lead screw.

In an aspect, the spring member may be configured to bias the first engaging portion of the second member proximally when the second engaging portion is threadably coupled to the lead screw.

In another aspect, the lead screw may have a proximal portion having a non-threaded surface.

In yet another aspect, the second member may have a tab extending radially inward, and the third member may define a groove defined along a length thereof. The tab may be configured to slidably engage the groove to inhibit rotation of the third member.

In still yet another aspect, the first member of the trocar assembly may be axially fixed with the tubular shaft.

In still yet another aspect, the second member may be disposed within the first member and the trocar of the third member may extend out of the first member when the trocar assembly is in the retracted configuration.

In accordance with another aspect of the disclosure, an adapter assembly for use with a surgical stapling instrument includes a tubular shaft and a trocar assembly. The tubular shaft supports a shell assembly of the surgical stapling instrument at a distal portion of the tubular shaft. The trocar assembly is attachable to an anvil assembly of the surgical stapling instrument. The trocar assembly is transitionable between an extended configuration and a retracted configuration. The trocar assembly includes a lead screw adapted to be coupled to an actuator for rotational input, a first member rotatably supporting the lead screw while inhibiting axial displacement of the lead screw, a second member threadably coupled to the lead screw such that rotation of the lead screw causes axial displacement of the second member, and a third member including a trocar configured to detachably engage the anvil assembly of the surgical stapling instrument. At least a portion of the third member is slidably disposed within the second member. The second member is slidable relative to the first member between a first position, in which, the third member is operatively engaged with the lead screw and a second position, in which, the third member is operatively disengaged from the lead screw.

In another aspect, the tubular shaft may include a first tubular member and a second tubular distal of the first tubular member. The second tubular member may be detachably supported with the first tubular member.

In yet another aspect, the second tubular member of the tubular shaft may be dimensioned to receive the trocar of the trocar assembly therethrough.

In still yet another aspect, the third member of the trocar assembly may be rotatably fixed with the second member.

In still yet another aspect, the second member of the trocar assembly may include a spring member interconnecting the second member and the third member.

In still yet another aspect, the lead screw may include a proximal end portion having a smooth surface.

BRIEF DESCRIPTION OF DRAWINGS

An adapter assembly for use with a surgical stapling instrument is disclosed herein with reference to the drawings, wherein:

FIGS. 3 and 4 are perspective views of a trocar assembly of the surgical stapling instrument of FIG. 1 in accordance with the disclosure;

FIG. 5 is an enlarged view of the indicated area of detail of FIG. 4;

FIG. 6 is a perspective view of an intermediate member of the trocar assembly of FIG. 3;

FIG. 7 is a side cross-sectional view of the trocar assembly of FIG. 3 taken along section line 7-7 of FIG. 3, illustrating the trocar assembly in an extended configuration;

FIG. 8 is a perspective view of the trocar assembly of FIG. 7 in an intermediate configuration;

FIG. 9. is a side cross-sectional view of the trocar assembly of FIG. 8 taken along section line 9-9 of FIG. 8;

FIG. 10 is a perspective view of the trocar assembly of FIG. 3 in a fully retracted configuration;

FIG. 11 is a cross-sectional view of the trocar assembly of FIG. 10 taken along section line 11-11 of FIG. 10;

FIG. 14 is a perspective view of the adapter assembly of FIG. 12 with a distal tube removed; and FIG. 15 is an enlarged perspective view of the indicated area of detail of FIG. 14.

DETAILED DESCRIPTION

Figure 1:
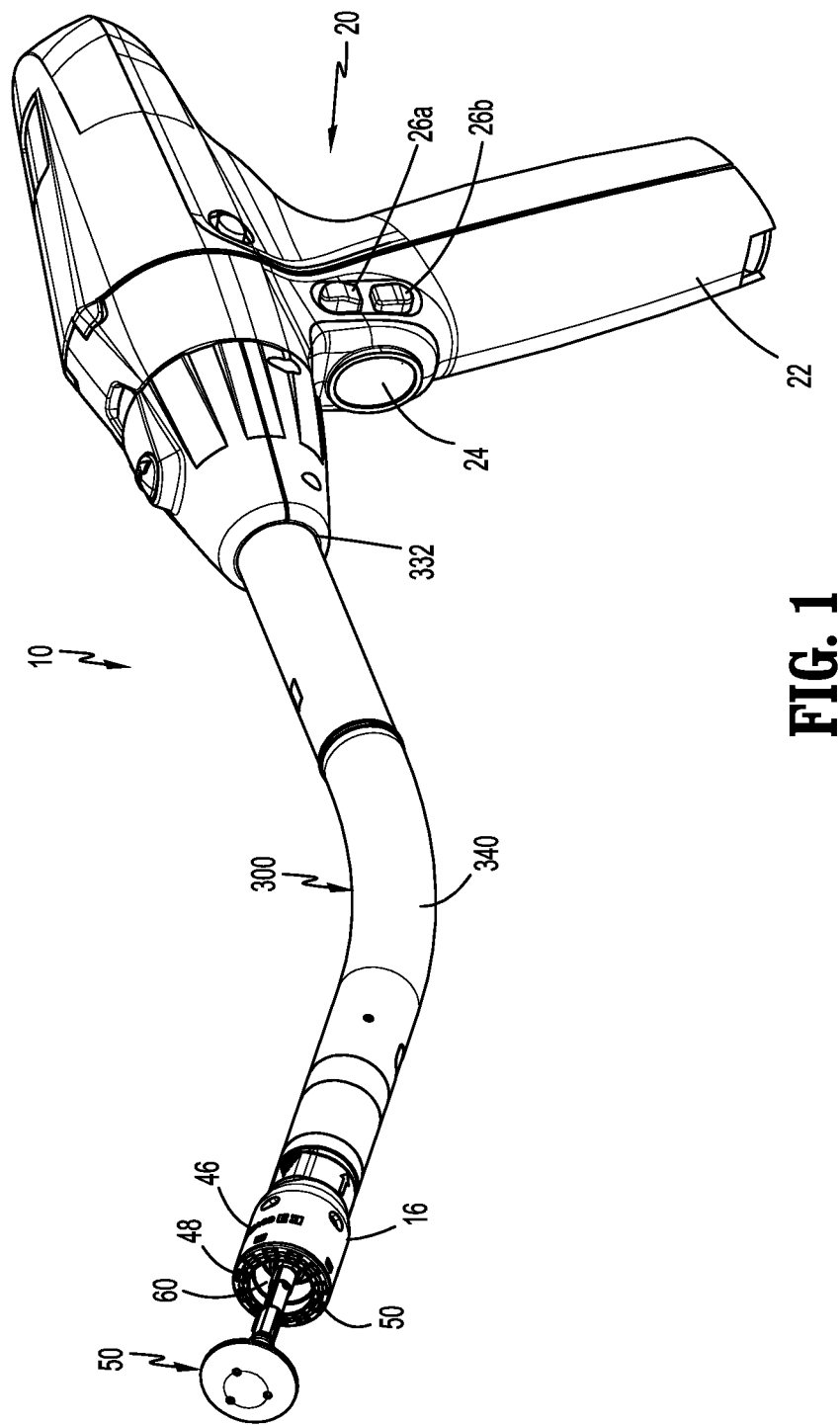
FIG. 1 is a perspective view of a surgical stapling instrument in accordance with the disclosure.

A surgical stapling instrument is described in detail with reference to the drawings, wherein like reference numerals designate corresponding elements in each of the several views. As used herein, the term "distal" refers to that portion of the instrument, or component thereof which is farther from the user during customary use of the instrument while the term "proximal" refers to that portion of the instrument or component thereof which is closer to the user during customary use of the instrument.

With reference to FIGS. 1-4, a trocar assembly for use with a surgical instrument, in the form of a surgical stapling instrument 10 is shown generally as 500. The trocar assembly 500 has a telescopic configuration that is transitionable between retracted and extended configurations, thereby facilitating sterilization and reprocessing of the surgical stapling instrument 10. For example, such a configuration enables repositioning of seal members (not shown) to facilitate sterilization or reprocessing of the surgical stapling instrument 10. The surgical stapling instrument 10 is a circular stapling instrument including a handle assembly 20, an adapter assembly 300 extending distally from the handle assembly 20 and including the trocar assembly 500 in accordance with the disclosure, a shell assembly 16 supported on a distal portion of the adapter assembly 300, and an anvil assembly 50 operatively coupled to the handle assembly 20.

The handle assembly 20 is illustrated as a powered assembly and includes a stationary grip 22, an actuation button 24 for controlling firing of staples (not shown) from an annular staple cartridge 48 of the shell assembly 16, and approximation buttons 26a, 26b for controlling axial displacement of the anvil assembly 50 towards and away from the shell assembly 16. For a detailed description of the structure and function of exemplary powered handle assemblies, reference may be made to U.S. Patent Application Publication Nos. 2020/0015820 and 2019/0343517, the entire contents of which are incorporated herein by reference. Although the disclosure illustrates a powered assembly, it is envisioned that the advantages of the disclosure as described in detail below are also applicable to surgical stapling instruments having manually operated handle and body assemblies or robotically actuated surgical instruments. U.S. Pat. No. 7,303,106 (the '106 patent) discloses an example of a surgical stapling instrument including a manually actuated handle assembly and is incorporated herein by reference in its entirety. It is also envisioned that the disclosed stapling instrument can be supported on a robotic system and need not include a handle assembly.

With continued reference to FIGS. 1-4, the adapter assembly 300 includes an interface portion 332 detachably coupled to the handle assembly 20, a tubular shaft 340 extending distally from the interface portion 332, and the trocar assembly 500 operatively supported within the adapter assembly 300. The shell assembly 16 is supported on a distal portion of the tubular shaft 340 and includes a shell housing 46 and an annular staple cartridge 48 that defines annular rows of staple receiving pockets 50. In particular, the shell assembly 16 may be releasably coupled to the distal portion of the tubular shaft 340 to facilitate replacement of the annular staple cartridge 48 after each use.

Each of the staple receiving pockets 50 supports a staple (not shown) that can be fired from the annular staple cartridge 48 via actuation of the actuation button 24 of the handle assembly 20 and formed within the staple forming pockets 25 of a staple forming surface 29 of an anvil head 28 of the anvil assembly 50. The shell housing 46 of the shell assembly 16 defines an annular cavity 60. The annular cavity 60 supports a staple pusher (not shown) and an annular knife (not shown) such that the staple pusher and the annular knife are movable in relation to the annular staple cartridge 48 to eject the staples from the annular staple cartridge 48 and to dissect or cut tissue positioned within an annulus defined by the annular staple cartridge 48. For a detailed description of the structure and function of the exemplary shell assemblies reference may be made to the '106 patent, the entire contents of which is incorporated herein by reference.

Figure 2:
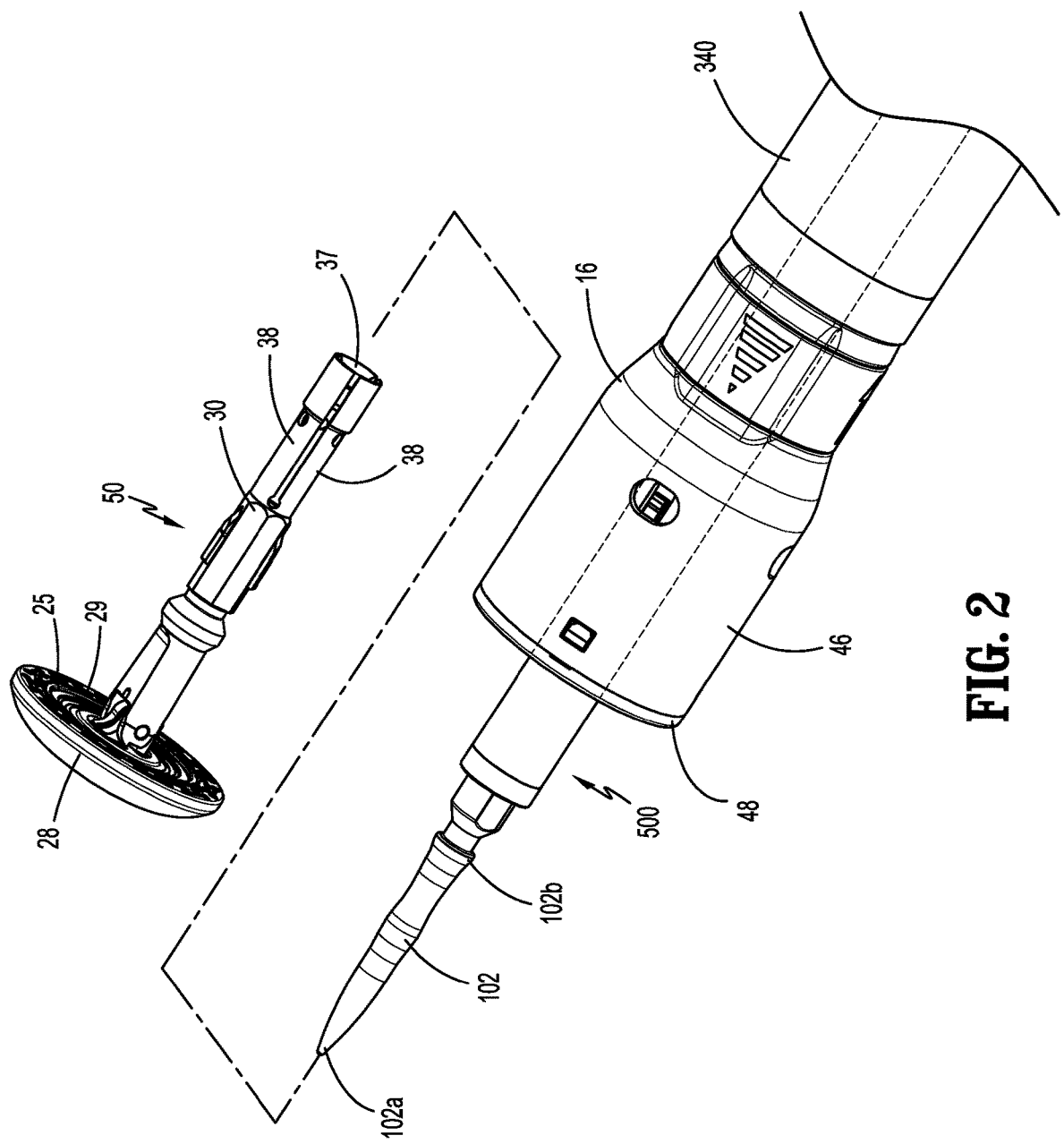
FIG. 2 is a perspective view of an anvil assembly and a shell assembly of the surgical stapling instrument of FIG. 1.
Figure 12:
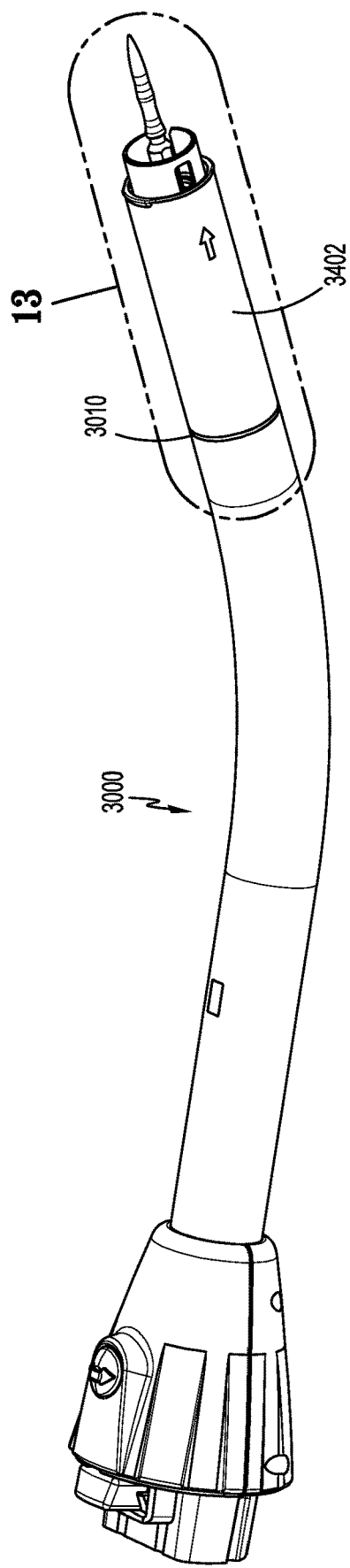
FIG. 12 is a perspective view of an adapter assembly for use with the surgical stapling instrument of FIG. 1 in accordance with the disclosure.
Figure 13:
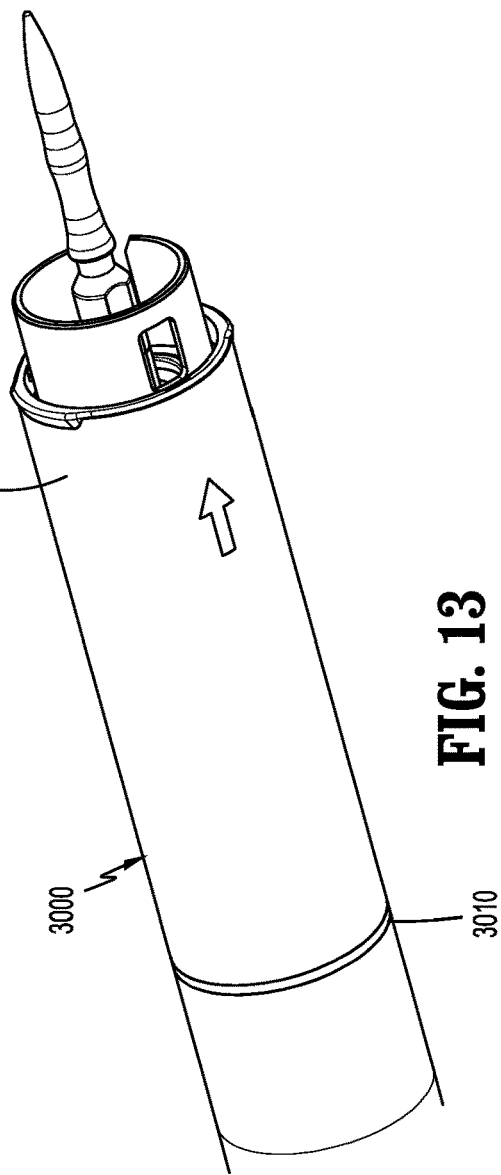
FIG. 13 is an enlarged perspective view of the indicated area of detail of FIG. 12.

With particular reference to FIG. 2, the anvil assembly 50 includes the anvil head 28 and an anvil center rod 30. The anvil head 28 includes the staple deforming surface 29 that includes staple deforming pockets 25. The anvil center rod 30 includes a plurality of resilient fingers 38 defining a longitudinal bore 37 that is dimensioned to receive and releasably engage a trocar 102 of the trocar assembly 500. In an aspect, the anvil head 28 may be pivotally coupled to the anvil center rod 30 and may be movable between an operative position for forming staples and a tilted, reduced profile position. The anvil assembly 50 may be releasably coupled to the trocar assembly 500 for concomitant axial displacement of the anvil assembly 50 relative to the shell assembly 16 (FIG. 1) by activating an actuator (not shown) such as, e.g., an electric motor, in the handle assembly 20 (FIG. 1). The trocar 102 includes a distal portion 102a that is tapered and a proximal portion 102b that has a diameter larger than a diameter of the distal portion 102a. The distal portion 102a is detachably received within the longitudinal bore 37 that is defined by the plurality resilient fingers 38 of the anvil assembly 50. Rotational input to the trocar assembly 500 (FIG. 3) transitions the anvil assembly 50 between a spaced apart configuration and an approximated configuration, in which, the staple deforming surface 29 of the anvil assembly 50 is in juxtaposed alignment with the annular staple cartridge 48.

With reference to FIGS. 3 and 4, the trocar assembly 500 includes a proximal member 510, an intermediate member 550 slidable relative to the proximal member 510, and a distal member 580 slidable relative to the intermediate member 550. In particular, the proximal, intermediate, and distal members 510, 550, 580 are concentrically arranged. The intermediate member 550 may be slidably received in the proximal member 510, and at least a portion of the distal member 580 is slidably received in the intermediate member 550. Under such a configuration, the trocar assembly 500 is transitionable between a fully extended configuration (FIG. 3) and a fully retracted configuration (FIG. 10). However, the trocar assembly 500 may be positioned in an intermediate configuration that is partially retracted or partially extended (FIG. 8).

With reference to FIGS. 5-7, the proximal member 510 includes proximal and distal end portions 520, 522 and defines a longitudinal channel 514 therein. In particular, a lead screw 120 is rotatably supported therein, e.g., the proximal end portion 520. The lead screw 120 includes an annular protrusion 129 configured to be received in a circular groove defined in an inner surface of the proximal member 510 to inhibit axial displacement of the lead screw 120 during rotation of the lead screw 120. The lead screw 120 is operatively coupled to an actuator (not shown) such as, e.g., an electric motor, in the handle assembly 20 (FIG. 1) for rotational input. For example, a cable (not shown) may interconnect the lead screw 120 and the actuator for rotational input. The cable may be formed of a flexible material to enable flexion of the cable in, e.g., radial and/or axial, directions. In this manner, the cable may accommodate the shape and contour of the adapter assembly 300. Rotation of the lead screw 120 causes axial displacement of the anvil assembly 50 as will be described.

The distal end portion 522 of the proximal member 510 defines an opening dimensioned to receive the intermediate member 550 therethrough to enable relative axial displacement of the intermediate member 550 within the longitudinal channel 514 of the proximal member 510.

With continued reference to FIGS. 5-7, the intermediate member 550 includes a tubular body 552 including an engaging portion 562 and a receiving portion 568 distal of the engaging portion 562. The engaging portion 562 defines a threaded bore 564 that threadably engages the lead screw 120. The receiving portion 568 defines a second longitudinal channel 569 extending along a length thereof. In particular, the second longitudinal channel 569 has a spring member 577 disposed therein. The second longitudinal channel 569 has a diameter greater than a diameter of the threaded bore 564. In addition, the second longitudinal channel 569 is dimensioned to receive at least a portion of the distal member 580. The distal end portion 559 of the intermediate member 550 further includes tabs 523 extending radially inward to engage a groove 582 defined in the distal member 580. For example, the tabs 523 may be diametrically opposed. Each groove 582 may extend along a length of the distal member 580. Under such a configuration, when the lead screw 120 threadably engages the engaging portion 562 of the intermediate member 550, the intermediate member 550 is axially displaced, as the tabs 523 inhibit rotation of the intermediate member 550.

With continued reference to FIGS. 5-7, the distal member 580 includes a body portion 582 and the trocar 102 extending distally from the body portion 582. The distal member 580 may be integrally formed. Alternatively, the distal member 580 may be monolithically formed. Further, it is contemplated that the trocar 102 may be detachably coupled to the body portion 582. In particular, the body portion 582 includes an engaging portion 586 defining a threaded bore 590 that threadably receives the lead screw 120. In addition, the engaging portion 586 is securely coupled to the spring member 577 in the second longitudinal channel 569 of the intermediate member 550. The spring member 577 is further securely coupled to the engaging portion 562 of the intermediate member 550. Under such a configuration, when the engaging portion 586 of the distal member 580 is disengaged from the lead screw 120, the spring member 577 biases the distal member 580 distally in the direction of arrow "D". In addition, the spring member 577 biases the intermediate member 550 proximally towards the non-threaded portion 121 (FIG. 7) of the lead screw 120 to allow the trocar 102 to be fully retracted. When the lead screw 120 threadably engages the threaded bore 590 of the distal member 580, the tabs 523 of the intermediate member 550 received in the groove 582 of the body portion 582 of the distal member 580 inhibits rotation of the distal member 580 and enables axial displacement of the distal member 580.

With reference now to FIGS. 7-9, when the lead screw 120 is rotated by activation of the actuator in the handle assembly 20, the lead screw 120 engages the threaded bore 564 of engaging portion 562 of the intermediate member 550, which, in turn, causes axial displacement of the intermediate member 550 in the direction of arrow "P". As the intermediate member 550 is retracted, the lead screw 120 is received through the spring member 577 interposed between the engaging portion 562 of the intermediate member 550 and the engaging portion 586 of the distal member 580. Further, the lead screw 120 comes into threadable engagement with the engaging portion 586 of the distal member 580, which, in turn, causes axial displacement of the distal member 580 in the direction of arrow "P."

With reference to FIGS. 10 and 11, further rotation of the lead screw 120 further causes axial displacement of the engaging portion 586 of the distal member 580 to a proximal-most position. At this time, a distal end portion 559 of the intermediate member 550 is disposed proximal of the distal end portion 522 of the proximal member 510, and the engaging portion 586 of the distal member 580 is proximal of the distal end portions 522, 559 of the proximal member 510 and the intermediate member 550. At this time, the spring member 577 is compressed between the engaging portion 586 of the distal member 580 and the engaging portion 562 of the intermediate member 550. In addition, a portion of the lead screw 120 extends into the body portion 582 of the distal member 580, and the trocar 102 is disposed distal of the proximal and intermediate members 510, 550. In this manner, when the actuator of the handle assembly 20 is activated such that the lead screw 120 is rotated in a direction of an arrow "C", the trocar assembly 500 is transitioned from the fully extended configuration (FIG. 3) to the fully retracted configuration (FIG. 10). When the lead screw 120 is rotated in a direction opposite of the arrow "C", the trocar assembly 500 is transitioned from the fully retracted configuration to the fully extended configuration. In particular, the spring member 577 biases the trocar 102 distally to interface with the anvil assembly 50 when the trocar assembly 500 is in the full extension, and the spring member 577 also biases the intermediate member 550 proximally towards the non-threaded portion 121 (FIG. 7) of the lead screw 120 to allow the trocar 102 to be fully retracted. In an aspect, it is contemplated that the trocar assembly 500 may include a latch or cam mechanism configured to retain the trocar 102 in a distal position when extended. Under such a configuration, the trocar assembly 500 in the retracted configuration provides working space in the adapter assembly 300, which, may be used to move other components such as, e.g., seals, to facilitate reprocessing and sterilization of the adapter assembly 300.

With reference to FIGS. 12-15, it is further contemplated that in order to facilitate reprocessing and/or sterilization of the adapter assembly 3000, a tubular member 3402 of the adapter assembly 3000 may be removable prior to reprocessing or sterilization in order to expose the interior of the adapter assembly 3000. In particular, the tubular member 3402 may be supported at a distal end portion of the adapter assembly 3000. In particular, the tubular member 3402 may be detachably coupled to the distal end portion 3010 of the adapter assembly 3000 through, e.g., threadable connection, snap-fit, bayonet fitting, etc. Alternatively, the tubular member 3402 may be secured by the shell assembly 16 (FIG. 1). In this manner, reprocessing or sterilization of the interior of the adapter assembly 3000 may be enhanced.

Initially, tubular tissue may be placed between the anvil head 28 and the shell assembly 16 to perform anastomosis. At this time, the surgical stapling instrument 10 may be in the spaced apart configuration (FIG. 3). The approximation button 26a may be pressed to transition the anvil head 28 of the anvil assembly 50 to the approximated configuration to clamp tissue between the anvil head 28 and the annular cartridge assembly 48. At this time, the actuator of the handle assembly is activated to provide rotational input to the lead screw 120. Rotation of the lead screw 120 provides axial displacement of the intermediate and distal members 550, 580 in the direction of the arrows "P", which, in turn, retracts the anvil head 28 to the approximated configuration. At this time, tissue is clamped between the anvil head 28 and the shell assembly 16. Thereafter, the actuation button 24 may be pressed to activate an actuator to perform stapling and cutting of tissue disposed between the anvil head 28 and the shell assembly 16. Thereafter, the clinician may press the approximation button 26b to transition the anvil head 28 to the spaced apart configuration. After the surgical procedure, the adapter assembly 300 may be reprocessed or sterilized for reuse. The anvil assembly 50 may be detached from the trocar assembly 500 and the approximation button 26a may be pressed to transition the trocar assembly 500 to the fully retracted configuration such that the adapter assembly 300 provides working space for displacement of seals and improved accessability to the interior of the adapter assembly 300. In addition, the distal tube 3402 may also be removed to further improve accessibility to the interior of the adapter assembly 300. The distal tube 3402 may be reprocessed or sterilized for reuse or may be replaced.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:
    an anvil assembly including an anvil head and an anvil center rod extending proximally from the anvil head;
    a shell assembly including an annular staple cartridge including a plurality of staples; and
    an adapter assembly including:
        a tubular shaft supporting the shell assembly at a distal portion of the tubular shaft; and
        a trocar assembly transitionable between an extended configuration and a retracted configuration, the trocar assembly including:
            a lead screw adapted to be coupled to an actuator for rotational input;
            a first member rotatably supporting the lead screw;
            a second member operatively coupled to the lead screw such that rotation of the lead screw causes axial displacement of the second member relative to the first member; and
            a third member slidable relative to the second member, the third member including a trocar detachably engageable with the anvil center rod for axial displacement therewith, the third member transitionable between an engaged state, in which, the third member is operatively coupled to the lead screw such that rotation of the lead screw causes axial displacement of the third member relative to the second member, and a disengaged state, in which, the third member is operatively disengaged from the lead screw, wherein rotation of the lead screw transitions the trocar assembly between the extended configuration and the retracted configuration.

2. The surgical stapling instrument according to claim 1, wherein the first, second, and third members are concentrically arranged.

3. The surgical stapling instrument according to claim 1, wherein the lead screw includes an annular protrusion configured to be received in a circular groove defined in an inner surface of the first member to inhibit axial displacement of the lead screw during rotation thereof.

4. The surgical stapling instrument according to claim 1, wherein the second member includes a first engaging portion that defines a first threaded bore, the first threaded bore being engageable with the lead screw.

5. The surgical stapling instrument according to claim 4, wherein the first engaging portion of the second member is disposed in a proximal end portion of the second member.

6. The surgical stapling instrument according to claim 4, wherein the second member further includes a receiving portion distal of the engaging portion, the receiving portion defining a first channel configured to slidably receive the third member therein.

7. The surgical stapling instrument according to claim 6, wherein the third member includes a second engaging portion slidably disposed within the second member, the second engaging portion defining a second threaded bore configured to threadably engage the lead screw.

8. The surgical stapling instrument according to claim 7, wherein the second member includes a spring member interconnecting the first engaging portion of the second member and the second engaging portion of the third member.

9. The surgical stapling instrument according to claim 8, wherein the spring member is configured to bias the third member distally when the second engaging portion of the third member is disengaged from the lead screw.

10. The surgical stapling instrument according to claim 9, wherein the spring member is configured to bias the first engaging portion of the second member proximally when the second engaging portion is threadably coupled to the lead screw.

11. The surgical stapling instrument according to claim 10, wherein the lead screw has a proximal portion having a non-threaded surface.

12. The surgical stapling instrument according to claim 1, wherein the second member has a tab extending radially inward, and the third member defines a groove defined along a length thereof, the tab configured to slidably engage the groove to inhibit rotation of the third member.

13. The surgical stapling instrument according to claim 1, wherein the first member of the trocar assembly is axially fixed with the tubular shaft.

14. The surgical stapling instrument according to claim 1, wherein the second member is disposed within the first member and the trocar of the third member extends out of the first member when the trocar assembly is in the retracted configuration.

15. An adapter assembly for use with a surgical stapling instrument comprising:
  a tubular shaft supporting a shell assembly of the surgical stapling instrument at a distal portion of the tubular shaft; and
  a trocar assembly attachable to an anvil assembly of the surgical stapling instrument, the trocar assembly transitionable between an extended configuration and a retracted configuration, the trocar assembly including:
    a lead screw adapted to be coupled to an actuator for rotational input;
    a first member rotatably supporting the lead screw while inhibiting axial displacement of the lead screw;
    a second member threadably coupled to the lead screw such that rotation of the lead screw causes axial displacement of the second member; and
    a third member including a trocar configured to detachably engage the anvil assembly of the surgical stapling instrument, at least a portion of the third member slidably disposed within the second member,
  wherein the second member is slidable relative to the first member between a first position, in which, the third member is operatively engaged with the lead screw and a second position, in which, the third member is operatively disengaged from the lead screw.

16. The adapter according to claim 15, wherein the tubular shaft includes a first tubular member and a second tubular distal of the first tubular member, the second tubular member being detachably supported with the first tubular member.

17. The adapter according to claim 16, wherein the second tubular member of the tubular shaft is dimensioned to receive the trocar of the trocar assembly therethrough.

18. The adapter according to claim 16, wherein the third member of the trocar assembly is rotatably fixed with the second member.

19. The adapter according to claim 16, wherein the second member of the trocar assembly includes a spring member interconnecting the second member and the third member.

20. The adapter according to claim 16, wherein the lead screw includes a proximal end portion having a smooth surface.

* * * * *